(12) United States Patent
Van Hee et al.

(10) Patent No.: US 9,018,178 B2
(45) Date of Patent: Apr. 28, 2015

(54) METHOD FOR THE TREATMENT OF FOOD, FEED AND AGRICULTURAL PRODUCTS WITH A POLYENE ANTIFUNGAL COMPOUND

(75) Inventors: Pim Van Hee, Delft (NL); Laurentius Cornelis Adrianus Van Santen, Stompwijk (NL); John Mark Faragher, Richfield, WI (US)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/669,617

(22) PCT Filed: Jul. 17, 2008

(86) PCT No.: PCT/EP2008/059349
§ 371 (c)(1),
(2), (4) Date: Jun. 28, 2010

(87) PCT Pub. No.: WO2009/010547
PCT Pub. Date: Jan. 22, 2009

(65) Prior Publication Data
US 2010/0292315 A1    Nov. 18, 2010

Related U.S. Application Data

(60) Provisional application No. 60/929,944, filed on Jul. 19, 2007.

(30) Foreign Application Priority Data

Jul. 30, 2007 (EP) .................................... 07113455
Aug. 16, 2007 (EP) .................................... 07114406

(51) Int. Cl.
A01N 43/04     (2006.01)
A61K 31/70     (2006.01)
A01N 43/02     (2006.01)
A61K 31/335    (2006.01)
A01N 43/90     (2006.01)

(52) U.S. Cl.
CPC ..................... *A01N 43/90* (2013.01)

(58) Field of Classification Search
USPC .................................................... 514/450, 31
See application file for complete search history.

(56) References Cited

U.S. PATENT DOCUMENTS

| | | | |
|---|---|---|---|
| 4,148,891 A | 4/1979 | Smink | |
| 5,552,151 A | 9/1996 | Noordam et al. | |
| 5,597,598 A | 1/1997 | Van Rijn et al. | |
| 5,895,680 A * | 4/1999 | Cirigliano et al. | 426/326 |
| 5,962,510 A | 10/1999 | De Haan et al. | |
| 6,150,143 A | 11/2000 | Raghoenath et al. | |
| 6,655,081 B1 | 12/2003 | Stark et al. | |
| 7,816,332 B2 | 10/2010 | Stark et al. | |
| 2006/0222746 A1 * | 10/2006 | Cirigliano et al. | 426/335 |

FOREIGN PATENT DOCUMENTS

| | | |
|---|---|---|
| EP | 0 490 564 | 6/1992 |
| EP | 0 608 944 | 8/1994 |
| EP | 0 678 241 | 10/1995 |
| EP | 0 988 798 | 3/2000 |
| WO | WO 2005/097063 | 10/2005 |

OTHER PUBLICATIONS

Ansel's Pharmaceuticals (1995) p. 258.*
International Search Report for PCT/EP2008/059349 mailed Dec. 11, 2008.
Grafen et al., "Lochkorrosion an Nichtrostenden Stahlen", *Materials and Corrosion*, vol. 47, No. 1, Jan. 1996, pp. 16-26, XP002485163.
"The Application of Biological Preservative in Dairy Products", Food Research and Development, vol. 28, No. 1, pp. 162-165 (2007), English translation thereof.
Chunlai Lin (Bangshuidao Food Group Dalian Chunhe Food Co. Ltd Dalian 116011), "Application of Several Preservatives in Meat Products." Submitted with English Translation thereof.

* cited by examiner

*Primary Examiner* — Layla Soroush
(74) *Attorney, Agent, or Firm* — Miles & Stockbridge PC

(57) ABSTRACT

The present invention provides an aqueous antifungal composition comprising a polyene antifungal compound and a thickening agent. The composition can be used in the protection against the development of fungi on food, feed and agricultural products.

10 Claims, No Drawings

METHOD FOR THE TREATMENT OF FOOD, FEED AND AGRICULTURAL PRODUCTS WITH A POLYENE ANTIFUNGAL COMPOUND

This application is the U.S. national phase of International Application No. PCT/EP2008/059349 filed 17 Jul. 2008 which designated the U.S. and claims priority to U.S. Provisional Application No. 60/929,944 filed 19 Jul. 2007 and EP Application Nos. 07113455.5 filed 30 Jul. 2007 and 07114406.7 filed 16 Aug. 2007, the entire contents of each of which are hereby incorporated by reference.

FIELD OF THE INVENTION

The present invention relates to a method for the treatment of food, feed and agricultural products with an antifungal compound.

BACKGROUND OF THE INVENTION

Prevention of mould growth is an important topic to the food, feed and agricultural industry, as fungal spoilage can lead to considerable economic losses. Some products can be considered as good substrates for fungal growth. Cheeses and sausages are examples of such products. Apart from the negative appearance of fungal growth on food, feed and agricultural products, fungal spoilage can also become a health risk. It is known that some mould species that contaminate food, feed and agricultural products can produce mycotoxins which can penetrate into the products (see Frisvad and Thane (1995)). Consequently, superficial removal of moulds gives no guarantee of safety to the consumer.

For more than 30 years, natamycin has been used to prevent growth of moulds and yeasts on a variety of products including food products such as cheeses and sausages. Natamycin is a natural polyene macrolide antifungal compound produced by fermentation of bacteria such as *Streptomyces natalensis*. Natamycin has an extremely effective and selective mode of action against a very broad spectrum of common food spoilage yeasts and moulds with most strains being inhibited by concentrations as low as 1-15 ppm. Despite its long-term use, the development of resistant strains against natamycin has not been reported to date unlike the chemical organic acid sorbate and propionate preservatives for which a number of resistant yeasts and moulds have been detected and reported.

There exist several ways by which food, feed and agricultural products can be treated with natamycin. For example, natamycin can be added to an emulsion of a polymer in water, mostly polyvinyl acetate, which can be applied as a coating on a product such as for example cheese (see Daamen and Berg (1985)). Products, e.g. cheeses or sausages, can also be treated by immersion or spraying with a suspension of natamycin in water (see Morris and Castberg (1980)). Usually polymer emulsions for coating purposes contain 0.01 to 0.05% (w/v) of natamycin, while aqueous suspensions for immersion treatments contain 0.1 to 0.2% (w/v) of natamycin and aqueous suspensions for spraying contain 0.1 to 1.5% (w/v) of natamycin, respectively.

Natamycin is on the market under the brand name of DEL-VOCID®, a powder composition containing natamycin and a thickening agent, e.g. xanthan gum. Currently, aqueous natamycin compositions are prepared by weighing the powder and mixing it with water. Salt is added to the aqueous natamycin compositions to improve the drying properties of the composition on the product and to increase microbiological stability of the compositions. This results in a final antifungal composition having a pH of around 6 that can effectively be used in the prevention of fungal spoilage (see EP 0 867 124). However, the use of the composition gives rise to significant problems with respect to corrosion of process equipment such as machines used in food processing plants.

DESCRIPTION OF THE INVENTION

The present invention now provides salt-free compositions, preferably aqueous salt-free compositions, comprising an antifungal compound that on the one hand prevent and/or avoid corrosion of process equipment used during the treatment of food, feed or agricultural products with antifungal compositions e.g. antifungal aqueous compositions, while on the other hand protect the food, feed, or agricultural products against the development of moulds and yeasts, i.e. they prevent fungal growth on and/or in the products. Moreover, the salt-free aqueous compositions are convenient ready-to-use and easy-to-use liquid compositions. They obviate the need to repeatedly prepare aqueous compositions by laborious and meticulous weighing and avoid the nuisance of dust problems and lump formation arising during blending and weighing. A further advantage of the salt-free aqueous compositions of the invention is their increased microbiological stability when compared to compositions as disclosed in the prior art, e.g. EP 0 867 124. As a result of their increased microbiological stability combined with their excellent physical and chemical stability, they advantageously can be stored for prolonged periods of time and therefore have an increased shelf life.

In a first aspect the invention relates to compositions comprising an antifungal compound, preferably a polyene antifungal compound. In a preferred embodiment the antifungal compositions are aqueous. Preferably, the compositions of the invention are free of corrosive ingredients. Corrosive ingredients include, but are not limited to, strong acids such as sulphuric acid, nitric acid and hydrochloric acid; strong bases such as sodium hydroxide and potassium hydroxide; oxidizing agents and halogen containing compounds including halogen salts. Halogen containing compounds as used herein include, but are not limited to, chloride salts such as sodium chloride, potassium chloride, calcium chloride, zinc chloride and magnesium chloride, bromide salts such as sodium bromide and potassium bromide, chlorate salts, hypochlorite salts and chloride containing acids. In an embodiment the compositions of the invention are free of halogen salts. In a preferred embodiment the compositions of the invention are free of chloride salts, preferably free of sodium chloride or potassium chloride. It is to be understood that the compositions of the invention may comprise low amounts of corrosive ingredients, as long as the amount or concentration of the corrosive ingredients does not lead to corrosion of e.g. process equipment. Corrosion depends among others on the type of material of the process equipment, the type and construction of the process equipment, the type of salt, the concentration of the salt, the pH, the temperature, the presence of soluble as well as insoluble impurities, the flow rate, etc. A person skilled in the art is capable of calculating the amount or concentration of corrosive ingredients that for a given material under given conditions and circumstances is a threshold value above which corrosion of the given material will occur. By way of example, for stainless steel of the type 1.4404 at a pH in the range of 3.5 to 8.0 and a temperature of 5° C. to 25° C. the amount of sodium chloride should not exceed 0.5% (w/w). Above this amount the sodium chloride gets corrosive.

Polyene antifungal compounds that can be used in the compositions of the invention include, but are not limited to, natamycin, nystatin, lucensomycin and amphotericin B, with natamycin being preferred. Compositions comprising two or more different polyene antifungal compounds are also part of the present invention. The compositions of the present invention comprise a polyene antifungal compound in an amount of from 50 ppm to 400,000 ppm, preferably in an amount from 100 ppm to 100,000 ppm, more preferably in an amount of from 200 ppm to 25000 ppm, even more preferably in an amount of from 400 ppm to 10000 ppm, particularly in an amount of from 600 ppm to 5000 ppm and more particularly of from 800 ppm to 2000 ppm.

In a further embodiment the compositions of the present invention comprise at least a thickening agent. Suitable thickening agents include, but are not limited to, carboxymethyl cellulose, carboxyethyl cellulose, xanthan gum, guar gum, Arabic gum, tragacanth gum, gellan gum, locust bean gum, carrageenan gum, rhamxan gum, alginate, starch, polyvinyl acetate, hydroxypropylmethyl cellulose, hydroxypropyl cellulose, methyl cellulose, polyvinyl alcohol, polyethylene glycol and polypropylene glycol. Xanthan gum is a preferred thickening agent in the compositions of the present invention. Preferably, thickening agent is present in an amount of from 0.02% to 10% (w/w), more preferably in an amount of from 0.05% to 4% (w/w), even more preferably in an amount of from 0.075% to 2% (w/w) and particularly in an amount of from 0.1% to 1% (w/w). Compositions comprising two or more different thickening agents are also part of the present invention.

In a further embodiment the compositions of the present invention comprise an acidic compound. Suitable acidic compounds include, but are not limited to, citric acid, propionic acid, acetic acid, benzoic acid, cinnamic acid, diacetic acid, hops acid and sorbic acid, with citric acid being preferred. Different acids may be present in the compositions of the invention. In an embodiment the compositions of the present invention comprise acid, preferably citric acid, in an amount of from 0.05% to 5% (w/w), preferably in an amount of from 0.075% to 3% (w/w), more preferably in an amount of from 0.1% to 1% (w/w) and particularly in an amount of from 0.2% to 0.8% (w/w).

In a further embodiment, the compositions of the invention also comprise lactate such as potassium lactate, sodium lactate, lactic acid or any other lactate source. The lactate should be present in an amount of from 0.05% to 7.5% (w/w), preferably in an amount of from 0.15% to 5% (w/w), more preferably in an amount of from 0.2% to 2% (w/w) and particularly in an amount of from 0.3% to 0.6% (w/w).

Other compounds that may be present in the compositions of the invention include, but are not limited to, additional antimicrobial compounds, flow agents such as silicon dioxide, surfactants such as SDS and Triton, and buffering agents such as a phosphate buffer.

The composition of the present invention have a pH of from 1.5 to 5.5, preferably of from 2 to 5 and particularly of from 2.5 to 4.5.

The compositions of the present invention have a viscosity of from 25 mPas to 20,000 mPas, preferably of from 50 mPas to 5000 mPas, more preferably of from 75 mPas to 2500 mPas, particularly of from 150 mPas to 1000 mPas and more particularly of from 200 mPas to 500 mPas.

In a specific embodiment the compositions of the present invention are stable. The term "stable" as used herein means that at least an amount of antifungal compound, e.g. natamycin, sufficient for the intended commercial application is retained in the composition. In a preferred embodiment a composition is considered stable if at least about 50%, preferably at least about 60%, more preferably at least about 70%, more preferably at least about 80%, more preferably at least about 90%, even more preferably at least about 92% and particularly at least about 95% of the amount of the antifungal compound, e.g. natamycin, is retained after storage for at least 12 weeks, preferably at least 15 weeks, more preferably at least 18 weeks and particularly at least 20 weeks at a temperature of 20° C. (or equivalent conditions at an elevated or lowered temperature). Stable compositions are those which retain their chemical and/or physical stability, preferably their chemical stability, under these storage conditions. As used herein, the term "chemical stability" means that degradation of the antifungal compound, e.g. natamycin, in the composition by chemical pathways such as oxidation, reduction, hydrolysis or enzymatic action, for example, does not exceed an acceptable level, i.e. the amount of the antifungal compound, e.g. natamycin, in the composition does not diminish by more than about 50%, preferably more than about 40%, more preferably more than about 30%, more preferably more than about 20%, even more preferably more than about 10%, even more preferably more than about 8%, particularly more than about 5%, when stored under the storage conditions indicated above, as compared to the amount of the antifungal compound in the composition at time t=0 (e.g., prior to storage). Compositions which do not result in diminished amounts of the antifungal compound under these conditions evidence the fact that such compositions will possess excellent long term storage stability under ambient conditions. The term "physical stability" as used herein means that the antifungal compound, e.g. natamycin, in the composition retains a uniform and homogeneous distribution enough for its practical use in the absence of conventional agitation, shaking or mixing. In particular, a composition is considered physically stable if no more that about 70%, preferably no more than about 50%, more preferably no more than about 30%, even more preferably no more than about 20% and particularly no more than about 10% of the antifungal compound, e.g. natamycin, is settled out after storage for 1 week at a temperature of 20° C. (or equivalent conditions at an elevated or lowered temperature). Especially preferred compositions are those which also have microbiological stability. The term "microbiological stability" (also called microbial stability) as used herein means that the compositions so described do not support vegetative cell growth to unacceptable levels. In other words, when the compositions at t=0 have a microbiological cell count of about 1,000 CFU/ml, the compositions have a microbiological cell count of less than 100,000 CFU/ml, preferably less than 10,000 CFU/ml, more preferably less than 5,000 CFU/ml and particularly about or even less than 1,000 CFU/ml, during storage for at least 12 weeks at a temperature of 25° C. (or equivalent conditions at an elevated or lowered temperature and/or humidity). To put it otherwise, the microbiological cell count in the compositions does not increase more than thousand fold, preferably not more than five hundredfold, more preferably not more than two hundredfold, even more preferably not more than hundredfold and particularly does not increase at all or even decreases, when the compositions are stored for at least 50 days, preferably at least 80 days, more preferably at least 100 days and particularly at least 140 days at a temperature of 25° C. Methods to measure chemical and physical stability, e.g. HPLC analyses; or microbiological stability, e.g. microbiological cell count assays, that are well known to a person skilled in the art can be used in the present invention. An example of a suitable microbiological cell count assay is described in the examples (see International Dairy Federation. Cheese and Cheese Rind Determination of Natamycin Content Method by Molecular Absorption Spectrometry and by High-Performance Liquid Chromatography; IDF Standard 140A; Brussels, Belgium, 1992).

Another aspect of the present invention lies in a composition according to the present invention that is capable of drying within an acceptable period of time when located on the surface of a substrate treated with the composition for antifungal prevention and/or treatment when a temperature of 20° C. and a relative humidity of 88% is maintained.

Substrates that can be treated with the compositions of the present invention can be perishable products. They may be solid, liquid or semi-liquid. Such products include, but are not limited to, food and feed products for man or animals. Food or feed product to which the compositions of the invention may typically be applied include, but are not limited to, cheese, cream cheese, shredded cheese, cottage cheese processed cheese, sour cream, dried fermented meat product including salamis and other sausages, wine, beer, yoghurt, juice and other beverages, salad dressing, cottage cheese dressing, dips, bakery products and bakery fillings, surface glazes and icing, spreads, pizza toppings, confectionery and confectionery fillings, olives, olive brine, olive oil, juices, tomato purees and paste, condiments, and fruit pulp and the like food products, as well as feed products, such as pet food, broiler feed fruits, etc. In addition substrates may also be agricultural products including vegetables, crops, fruits, bulbs, seeds and other agricultural products which are susceptible to attack by moulds.

So, a substrate, e.g. a food, feed, agricultural or other product, having applied thereto a composition according to the invention is another part of the present invention. The substrate may contain a coating comprising a composition according to the present invention. In a preferred embodiment the substrate is a dairy product such as a cheese product, e.g. shredded cheese, block cheese, sliced cheese stacks or cottage cheese, or a sausage product.

The compositions of the present invention can be aqueous ready-to-use compositions, but may also be aqueous concentrated compositions/suspensions or stock compositions/suspensions which before use have to be diluted with a suitable diluent such as water or a buffer system. Alternatively, the compositions of the invention can also be used to prepare coating emulsions.

The present application also provides the use of a composition according to the present invention for the treatment of a food, feed, agricultural or other product. A method for treating a food, feed, agricultural or other product by applying a composition according to the invention is another aspect of the invention. By application of the composition fungal infection of the food, feed, agricultural or other product is prevented. The compositions of the invention may be applied to the substrate by dipping, immersion, spraying, brushing, or may be directly added in case the substrate is a liquid or semi-liquid. The compositions may leave a coating, e.g. an antifungal coating, on the substrate they are applied to/on.

A method for preparing a composition as described herein is another aspect of the present invention. The method comprises adding natamycin, xanthan gum, citric acid and lactate either separately or as a powdered composition to water and mixing it, followed, if necessary, by adjustment of the pH, viscosity or both. If added separately, some or all of the separate compounds may be in powder form, but alternatively some or all may also be in liquid form.

In a further aspect the application therefore also provides a composition according to the invention that is a non-aqueous composition, e.g. a powder composition. Preferably, the powder composition comprises natamycin, xanthan gum, citric acid and lactate. Optionally, lactate can be replaced by citrate such as sodium citrate in the powder composition. For one thing the powder composition can be used in the method for preparing the liquid compositions of the present invention, for the other thing the powder composition can be made by drying or lyophilizing the liquid compositions of the present invention.

The food processing industry is one of the largest manufacturing industries worldwide. In typical food processing plants equipment of varying ages and constructed of different materials such as carbon steel, aluminum, stainless steel and plastics can be found. Often the equipment in this industry is in contact with environments that are high in salinity content. This can give rise to corrosion of the equipment. Corrosion, i.e. an attack on the material due to a chemical or electrochemical reaction with the surrounding medium, can be a serious enemy for many of the materials in a food processing plant. Due to the strict food quality requirements most plants select stainless steel as a main material of choice for their process equipment. Stainless steel is able to form a thin protective invisible coating on the metal surface which resists further oxidation or rusting. This is called passivation. The protective coating is created when oxygen combines with the chrome in the stainless steel to form chrome oxide. The formation of this film is instantaneous in an oxidizing atmosphere such as air, water, or other fluids that contain oxygen. Although stainless steel is known to be able to maintain a high level of performance, while keeping corrosion to a minimum, total annual costs accounted to corrosion are estimated at $2.1 billion in the food industry in the USA alone. To decrease costs associated with corrosion, e.g. pitting corrosion, rusting, crack corrosion or crevice corrosion, new high-corrosion-resistance stainless steel can be developed or stainless steel can be prepared under hygienic conditions to increase passivation. Both solutions are however time-consuming and are associated with high costs. The present invention now provides a different solution to the corrosion problem, particularly corrosion of process equipment occurring as a consequence of the treatment of food, feed or agricultural products with compositions comprising antifungal compounds. The antifungal compositions used to date comprise salts e.g. halogen salts e.g. chloride salts such as sodium chloride (see EP 0 867 124), as the addition of sodium chloride improves the (surface) drying properties of the composition on the products and also improves microbiological stability of the composition allowing it to be stored for a moderate period of time. As indicated above, high salt, e.g. chloride salt, content creates many problems, e.g. corrosion problems, in the plant environment. It has now been found that corrosion of process equipment used during the treatment of food, feed or agricultural products with an aqueous antifungal composition can be prevented by the use of an essentially chloride salt free aqueous antifungal composition. Surprisingly, this composition also has good drying properties as well as an excellent microbiological stability. Thus, in another aspect the application pertains to the use of an essentially chloride salt free aqueous antifungal composition to prevent and/or avoid corrosion of process equipment used during the treatment of food, feed or agricultural products with an aqueous antifungal composition. Preferably, the essentially chloride salt free composition is a composition according to the present invention. The composition particularly limits corrosion of stainless steel used for product-contact surfaces, e.g. tubing and piping, joints, tanks, machined parts used in pumps, valves, homogenizers, deaerators, process-monitoring instruments, flow meters, ingredient feeders, blenders, mixers, dryers, pasteurizers, heat exchangers, conveyors and foreign body detectors or nozzles. Due to the absence of salt in the antifungal compo-

EXAMPLES

Example 1

Behavior of Common Bacterial Contaminants in Liquid Natamycin Containing Compositions: Effect of Salt on Microbiological Stability The behavior of bacteria commonly present in factory environments in liquid aqueous natamycin containing formulations was studied. *Lactobacillus casei* (DSM strain 19999), *Lactobacillus plantarum* (DSM strain 19102), *Streptococcus lactis* (DSM strain 17854), *Citrobacter freundii* (DSM strain 41371), *Pseudomonas fluorescens* (DSM strain 3926) and *Listeria innocua* (DSM strain 16324) were cultured separately on Plate Count Agar (PCA, Difco 247940), mixed in equal numbers and subsequently inoculated in the relevant compositions (inoculation level: 1000 cfu/ml). All compositions comprised about 1700 ppm natamycin and 0.13% (w/w) xanthan gum and had a neutral pH (pH between 7.6 and 8.0). Their behavior during storage at 25° C. was followed in time by pourplating samples (and decimal dilutions thereof) onto PCA. In addition, the behavior of bacteria naturally present in the ingredients was studied by analyzing non-inoculated samples in the same way. Unacceptable growth of bacteria (spoilage) was defined as at least a factor 100 increase in their number.

The results, shown in Table 1, indicate that unacceptable growth of bacteria in non-inoculated as well as inoculated samples is observed in a chloride salt free, high pH composition within one day. The addition of 7.4% (w/w) chloride salt delays spoilage to 84 days.

Example 2

Behavior of Common Bacterial Contaminants in Liquid Natamycin Containing Compositions: Effect of Acids on Microbiological Stability The behavior of bacteria commonly present in factory environments in liquid aqueous natamycin containing formulations was studied. *Lactobacillus casei* (DSM strain 19999), *Lactobacillus plantarum* (DSM strain 19102), *Streptococcus lactis* (DSM strain 17854), *Citrobacter freundii* (DSM strain 41371), *Pseudomonas fluorescens* (DSM strain 3926) and *Listeria innocua* (DSM strain 16324) were cultured separately on PCA, mixed in equal numbers and subsequently inoculated in the relevant compositions (inoculation level: 1000 cfu/ml). All compositions comprised 1000 ppm natamycin and 0.08% (w/w) xanthan gum and had a pH varying between 4 and 5. Their behavior during storage at 25° C. was followed in time by pourplating samples (and decimal dilutions thereof) onto PCA. In addition, the behavior of bacteria naturally present in the ingredients was studied by analyzing non-inoculated samples in the same way. Unacceptable growth of bacteria (spoilage) was defined as at least a factor 100 increase in their number.

The results, presented in Table 2, indicate that the addition of citric acid and lactic acid prevents spoilage of the samples for more than 140 days at pH 4 and pH 4.5 in inoculated and non-inoculated samples and at pH 5 in non-inoculated samples. In inoculated samples, spoilage occurring at pH 5 within 2 days was prevented by the addition of 0.5% (w/w) sorbic acid (data not shown). The microbiological stability of compositions comprising about 1000 ppm natamycin, 0.08% (w/w) xanthan gum, citric acid and having a pH≥3.25 was comparable to that observed with compositions of pH 4 to 5, wherein citric acid and lactic acid was added (data not shown). In addition, replacement of lactic acid with acetic acid did not have an influence on microbiological stability (data not shown). Similar results were obtained when the xanthan gum concentration was 0.20% (w/w) instead of 0.08% (w/w) (data not shown). Similar results as given above were also obtained when unacceptable growth of bacteria (spoilage) was defined as at least a factor 1000 increase in their number (data not shown).

Example 3

Corrosiveness of Liquid Aqueous Natamycin Compositions by Observation

Liquid natamycin compositions were prepared according to the recipes depicted in the Table 3. The corrosiveness of the liquid compositions is tested by immersing three different types of stainless steel, i.e. 1.4306, 1.4404 and 1.4539 after EN 10088-1, in the liquid compositions at 20° C. The corrosiveness is analyzed by observing the appearance of the stainless steel in time. The results show that the corrosiveness of mixtures 2, 4 and 6 is higher than that of mixtures 1, 3 and 5. The mixtures without salts thus have a lower corrosiveness.

Example 4

Corrosiveness of Liquid Aqueous Natamycin Compositions by Electrochemical Measurements Moreover, the liquid natamycin compositions as prepared according to the recipes depicted in the Table 3 were subjected to electrochemical experiments (see Riedel et al. (2004) and Gräfen et al. (1996)). These were carried out with a potentiostat of the PCI4/300 type (Gamry Instruments) with 8 cm$^2$ samples under nitrogen with a potential increase rate of 600 mV/h. In the measurements the potential between a stainless steel sample and a counter electrode in the compositions was varied. In this set-up pitting corrosion was induced by anodic polarization ($U_{LD}$). The repassivation potential (also called pitting passivation potential ($U_{LP}$)) was then determined through reverse cathodic polarization. By comparing the $U_{LP}$ with the previously determined resting potential $U_K$ a clear evaluation of whether there is danger of pitting corrosion or not can be performed. Pitting corrosion occurs in these systems when the repassivation potential falls short of the resting potential. The larger this difference the more severe the pitting corrosion. Furthermore, pitting corrosion is more probable the smaller the difference between the resting potential $U_K$ and the pitting corrosion potential $U_{LD}$.

Besides these measurements, the redox potential was measured with an InLab 501 Redox Electrode and a MP 225 pH Meter (Mettler-Toledo). The difference between the pitting corrosion potential ($U_{LD}$) and the redox potential ($U_{redox}$) is another indicator of pitting corrosion. When the redox potential is significantly greater than the pitting potential, stable pitting corrosion can be trigged for the specific combination of stainless steel and liquid composition. The measurement method is performed according to the international standard as given in Standard test method for conducting cyclic potentiodynamic polarization measurements for localized corrosion susceptibility of iron-, nickel-, or cobalt-based alloys, ASTM designation G61-86, Annual Book of ASTM.

The corrosiveness of two different stainless steel types (1.4301 (ASTM designation 304) and 1.4404 (ASTM designation 316L)) that are commonly used in the food industry and one stainless steel type (1.4539 (ASTM designation 904L)) that is used in high technology applications and that is generally too expensive to be used in the food industry in the liquid compositions of the invention was tested with cyclic polarization measurements as described above. The temperature during the measurements was 30° C.; the gas application was wet air; and the volume of the media used in the measurements was 200 ml. The stainless steel material designation after EN 10088 was used. The pitting corrosion potentials, the redox potentials and the repassivation potentials for the six different compositions of Table 3 with the three different types of stainless steel (1.4306, 1.4404 and 1.4539) is given in Table 4. In summary, there are three conditions where no crevice and pitting corrosion occurs; $U_{LD}-U_K \geq 150$ mV; $U_{LP} \geq U_K$; and $U_{redox} \leq U_{LD}$.

No pitting potential up to 1100 mV was found for any of the three tested stainless steel materials with any of the compositions 1, 3 and 5. Consequently, there is no corrosion risk for the three tested stainless steel materials at the test conditions with the salt-free composition 1, 3 or 5. Contrary to compositions 1, 3 and 5, there is a risk for crevice and pitting corrosion for stainless steel materials used in the food-industry for salt containing compositions 2, 4 and 6. No pitting corrosion risk was observed for stainless steel type 1.4539. This type of stainless steel is not used in food industry due to its high costs. The lack of pitting corrosion in this type of stainless steel is probably due to the high amount of molybdenum in the material.

Ergo, in general there is a clear difference in the corrosion risk of stainless steel materials between salt containing and salt-free natamycin compositions. The former has corrosion risk, while the latter has none.

Example 5

Stability of Liquid Aqueous Antifungal Compositions

The chemical stability of several liquid aqueous antifungal compositions was determined by HPLC-analysis of natamycin. Table 5 depicts the compositions tested. The lactate used was potassium L-lactate, the citric acid used was citric acid monohydrate, and the sorbate used was potassium sorbate. To the compositions from Table 5 a commercially available natamycin powder was added to make a total of 100% (w/w). The compositions were stored in sealed vials and the chemical stability of the compositions was tested for up to 84 days at a temperature of 20° C. The stability of natamycin in the compositions is shown in Table 6. From Table 6 can be deducted that the natamycin stability is excellent in the chloride salt free compositions comprising natamycin, xanthan gum, citric acid, lactate and optionally sorbate (compositions 1 to 11). In the composition comprising only natamycin, xanthan gum and chloride salt and the composition comprising only natamycin and xanthan gum (compositions 12 and 13, respectively) natamycin was less stable, the amount natamycin decreased to around 90% of the value at t=0. The lower stability of compositions 12 and 13 could be attributed to instability due to microbial growth.

Example 6

Drying Properties of Liquid Aqueous Antifungal Compositions

The drying properties of the compositions from Table 3 were determined by the following measurement. The drying rate of the compositions was measured in time by placing them in a plastic cup with a diameter of 2.6 cm. The cups including 1.5 ml of the respective compositions was weighed in time. The percentage of the initial water content is shown as a function of time (see Table 7). Table 7 clearly shows that mixtures without salt dry faster than those that do contain salt.

TABLE 1

Effect of salt on microbiological stability of liquid natamycin containing compositions.

| | Composition of sample | | | Microbiological stability[a] |  |
|---|---|---|---|---|---|
| | | Acids (% w/w) | | | |
| | NaCl (% | citric | lactic | (days at 25° C.) | |
| Sample | pH | w/w) | acid | acid | non-inoc. | inoc. |
| 1 | 6 | 0 | 0 | 0 | 1 | 1 |
| 2 | 6 | 7.4 | 0 | 0 | 84 | 84 |

[a]Time (in days) to 100-fold increase

TABLE 2

Effect of acids on microbiological stability of liquid natamycin containing compositions.

| | Composition of sample | | | Microbiological stability[a] | |
|---|---|---|---|---|---|
| | | Acids (% w/w) | | | |
| | NaCl (% | citric | lactic | (days at 25° C.) | |
| Sample | pH | w/w) | acid | acid | non-inoc. | inoc. |
| 1 | 4.0 | 0 | 0.33 | 0.5 | >140 | >140 |
| 2 | 4.5 | 0 | 0.12 | 0.5 | >140 | >140 |
| 3 | 5.0 | 0 | 0.05 | 0.5 | >140 | 2 |

[a]Time (in days) to 100-fold increase

TABLE 3

Liquid natamycin compositions.

| Ingredients (% w/w) | mixture 1 | mixture 2 | mixture 3 | mixture 4 | mixture 5 | mixture 6 |
|---|---|---|---|---|---|---|
| Xanthan gum | 0.20 | 0.20 | 0.20 | 0.20 | 0.30 | 0.30 |
| Natamycin | 0.10 | 0.10 | 0.10 | 0.10 | 0.10 | 0.10 |
| NaCl | 0 | 10.0 | 0 | 10.0 | 0 | 10.0 |
| Citric acid $H_2O$ | 0 | 0 | 0.33 | 0.33 | 0.33 | 0.33 |
| Calcium lactate $5H_2O$ | 0 | 0 | 0.60 | 0.60 | 0.60 | 0.60 |

Water was added to each of these mixtures to a total of 100% w/w

TABLE 4

Pitting corrosion potentials, the redox potentials and the repassivation potentials of different stainless steel materials in liquid natamycin compositions.

| Composition | Material Number | $U_{Redox}$ (mV$_{AgCl}$) | $U_K$ (mV$_{AgCl}$) | $U_{LD}$ (mV$_{AgCl}$) | $U_{LP}$ (mV$_{AgCl}$) | $U_{LP}$-$U_K$ (mV$_{AgCl}$) | $U_{LD}$-$U_{Redox}$ (mV$_{AgCl}$) | $U_{LD}$-$U_K$ (mV$_{AgCl}$) |
|---|---|---|---|---|---|---|---|---|
| 1 | 1.4301 | 354 | −76 | none | — | no pitting | | |
|   | 1.4404 |     | −162 | none | — | no pitting | | |
|   | 1.4539 |     | −124 | none | — | no pitting | | |
| 2 | 1.4301 | 202 | −153 | 35 | −84 | 69 | −167 | 188 |
|   | 1.4404 |     | −144 | 155 | −33 | 111 | −47 | 299 |
|   | 1.4539 |     | −133 | 975 | 595 | 728 | 773 | 1108 |
| 3 | 1.4301 | 362 | −32 | none | — | no pitting | | |
|   | 1.4404 |     | −170 | none | — | no pitting | | |
|   | 1.4539 |     | −138 | none | — | no pitting | | |
| 4 | 1.4301 | 280 | −43 | −25 | −69 | −26 | −305 | 18 |
|   | 1.4404 |     | −128 | 76 | −18 | 110 | −204 | 204 |
|   | 1.4539 |     | −109 | 1153 | 1050 | 1159 | 873 | 1262 |
| 5 | 1.4301 | 394 | −139 | none | — | no pitting | | |
|   | 1.4404 |     | −101 | none | — | no pitting | | |
|   | 1.4539 |     | −20 | none | — | no pitting | | |
| 6 | 1.4301 | 390 | −170 | −4 | −80 | 90 | −394 | 166 |
|   | 1.4404 |     | −200 | 166 | −27 | 173 | −224 | 366 |
|   | 1.4539 |     | 20 | 1177 | 1069 | 1049 | 787 | 1157 |
| Condition for no pitting | | | | | | >0 | >0 | >150 |

TABLE 5

Liquid antifungal compositions for stability testing

| Composition | Xanthan gum (w/w) | lactate (w/w) | citric acid (w/w) | NaCl (w/w) | sorbate (w/w) | water (w/w) | pH |
|---|---|---|---|---|---|---|---|
| 1 | 0.08% | 0.49% | 0.33% | 0.00% | 0.00% | 99.0% | 4.0 |
| 2 | 0.08% | 0.49% | 0.12% | 0.00% | 0.00% | 99.2% | 4.5 |
| 3 | 0.08% | 0.49% | 0.05% | 0.00% | 0.00% | 99.3% | 5.0 |
| 4 | 0.08% | 0.49% | 0.17% | 0.00% | 0.49% | 98.7% | 5.0 |
| 5 | 0.14% | 0.49% | 0.30% | 0.00% | 0.00% | 98.9% | 4.0 |
| 6 | 0.14% | 0.49% | 0.13% | 0.00% | 0.00% | 99.0% | 4.4 |
| 7 | 0.14% | 0.49% | 0.05% | 0.00% | 0.00% | 99.1% | 5.0 |
| 8 | 0.20% | 0.48% | 0.33% | 0.00% | 0.00% | 98.7% | 4.0 |
| 9 | 0.20% | 0.49% | 0.13% | 0.00% | 0.00% | 98.9% | 4.5 |
| 10 | 0.20% | 0.49% | 0.05% | 0.00% | 0.00% | 99.0% | 5.0 |
| 11 | 0.20% | 0.49% | 0.18% | 0.00% | 0.49% | 98.4% | 5.0 |
| 12 | 0.13% | 0.00% | 0.00% | 7.40% | 0.00% | 92.3% | 7.6 |
| 13 | 0.14% | 0.00% | 0.00% | 0.00% | 0.00% | 99.7% | 8.0 |

TABLE 6

Stability testing of antifungal compositions.

| composition | t = 0 days | t = 0.5 days | t = 2 days | t = 7 days | t = 84 days |
|---|---|---|---|---|---|
| 1 | 994 | 999 | 1012 | 1047 | 993 |
| 2 | 1005 | 986 | 1022 | 1060 | 1042 |
| 3 | 1009 | 980 | 1012 | 1039 | 1026 |
| 4 | 997 | 980 | 1003 | 1042 | 1004 |
| 5 | 1753 | 1755 | 1790 | 1837 | 1820 |
| 6 | 1773 | 1752 | 1814 | 1864 | 1849 |
| 7 | 1776 | 1760 | 1801 | 1852 | 1810 |
| 8 | 2527 | 2475 | 2535 | 2611 | 2524 |
| 9 | 2553 | 2507 | 2555 | 2644 | 2600 |
| 10 | 2565 | 2517 | 2585 | 2655 | 2605 |
| 11 | 2534 | 2506 | 2573 | 2629 | 2583 |
| 12 | 1689 | 1679 | 1712 | 1754 | 1535 |
| 13 | 1824 | 1793 | 1800 | 1858 | 1714 |

TABLE 7

Drying properties of aqueous antifungal compositions by weight measurement.

| Composition | Weight at t = 0 min (w/w) | Weight at t = 146 min (w/w) | Weight at t = 315 min (w/w) | Weight at t = 393 min (w/w) | Weight at t = 1307 min (w/w) | Weight at t = 1625 min (w/w) | Weight at t = 1805 min (w/w) |
|---|---|---|---|---|---|---|---|
| 1 | 100 | 92.9 | 85.2 | 81.3 | 45.3 | 28.6 | 21.5 |
| 2 | 100 | 95.0 | 87.9 | 85.1 | 58.8 | 47.4 | 41.7 |
| 3 | 100 | 94.0 | 84.7 | 80.7 | 44.1 | 26.8 | 19.5 |
| 4 | 100 | 94.4 | 88.1 | 84.6 | 58.6 | 45.3 | 40.4 |
| 5 | 100 | 93.0 | 84.6 | 80.4 | 41.2 | 23.7 | 14.6 |
| 6 | 100 | 94.2 | 86.9 | 82.6 | 56.5 | 42.0 | 36.4 |

REFERENCES

Daamen C B G and Berg G van den (1985), Prevention of mould growth on cheese by means of natamycin, Voedingsmiddelentechnologie 18(2):26-29.

Frisvad J C and Thane U (1995), Mycotoxin production by food-borne fungi, Introduction to food-borne fungi, 4$^{th}$ edn. (ed. R. A. Samson et al.), 251-260.

Gräfen H and Kuron D (1996), Lochkorrosion an nichtrostenden Stählen (Pitting corrosion of stainless steels), Materials and Corrosion 47:16.

Morris H A and Castberg H B (1980), Control of surface growth on blue cheese using pimaricin, Cultured Dairy Products Journal 15(2):21-23.

Riedel G, Werner H and Friedrich S (2004), Lochkorrosion nichtrostender Stähle and hochlegierter Fe/Ni/Cr/Mo-Werkstoffe—Entwicklungsstufen and Untersuchungsverfahren (Pitting corrosion of stainless steels and highly alloyed Fe/Ni/Cr/Mo materials—stages of development and test methods), Materials and Corrosion 54:940.

The invention claimed is:

1. An aqueous antifungal composition comprising natamycin, in an amount of from 50 ppm to 400,000 ppm, xanthan gum in an amount of from 0.02% to 10% (w/w), citric acid in an amount of from 0.05% to 5% (w/w) and lactate in an amount of from 0.05% to 7.5% (w/w), wherein the composition chloride salt free and is stable after storage for at least 12 weeks at a temperature of 20° C.

2. A composition according to claim 1 having a pH of 1.5 to 5.5.

3. A composition according to claim 1 having a viscosity of from 25 mPas to 20,000 mPas.

4. A composition according to claim 1, further comprising at least one compound selected from the group consisting of additional antimicrobial compounds, flow agents, surfactants and buffering agents.

5. A food, feed or agricultural product having applied thereto a composition according to claim 1.

6. A product according to claim 5, wherein the product is a cheese or a sausage product.

7. A method for preparing a composition according to claim 1 which comprises adding natamycin, xanthan gum, citric acid and lactate either separately or as a powder composition to water and mixing it, followed, if necessary, by adjustment of the pH, viscosity or both.

8. The method of claim 7 comprising adding to water a powder composition comprising natamycin, xanthan gum, citric acid and lactate.

9. The composition according to claim 1, wherein said chloride salt free aqueous antifungal composition reduces corrosion of stainless steel compared to a composition containing chloride salt.

10. The composition of claim 1 consisting essentially of natamycin, xanthan gum, citric acid and lactate.

* * * * *